(12) United States Patent
Auger et al.

(10) Patent No.: US 11,071,574 B2
(45) Date of Patent: Jul. 27, 2021

(54) TWIST-DRIVABLE PIN ASSEMBLY

(71) Applicant: DEPUY IRELAND UNLIMITED COMPANY, Cork (IE)

(72) Inventors: Joshua Auger, Fort Wayne, IN (US); Patrick Cannon, Warsaw, IN (US); Jonathan Lee, Dallas, TX (US); Duncan Young, Leeds (GB)

(73) Assignee: DEPUY IRELAND UNLIMITED COMPANY, Cork (IE)

( * ) Notice: Subject to any disclaimer, the term of this patent is extended or adjusted under 35 U.S.C. 154(b) by 144 days.

(21) Appl. No.: 16/352,926

(22) Filed: Mar. 14, 2019

(65) Prior Publication Data

US 2019/0209219 A1  Jul. 11, 2019

Related U.S. Application Data

(63) Continuation of application No. 14/442,534, filed as application No. PCT/US2013/075724 on Dec. 17, 2013.

(30) Foreign Application Priority Data

Dec. 17, 2012  (GB) ..................................... 1222688

(51) Int. Cl.
*A61B 17/86* (2006.01)
*B25B 15/00* (2006.01)
(Continued)

(52) U.S. Cl.
CPC ........ *A61B 17/8615* (2013.01); *A61B 17/888* (2013.01); *B25B 15/004* (2013.01);
(Continued)

(58) Field of Classification Search
CPC . A61B 17/8615; A61B 17/888; A61B 17/861; A61B 17/8877; B25B 15/004;
(Continued)

(56) References Cited

U.S. PATENT DOCUMENTS 3,575,080 A  4/1971  Hannay
3,604,305 A  9/1971  Dreger
(Continued)

FOREIGN PATENT DOCUMENTS

CN  2168114 Y  6/1994
CN  1283255 A  2/2001
(Continued)

OTHER PUBLICATIONS

GB Search Report for Corresponding GB Application No. GB1222688.2, dated Mar. 14, 2013, 5 Pages.
(Continued)

*Primary Examiner* — Marcela I. Shirsat

(57) ABSTRACT

A twist-drivable pin assembly includes first and second drivers, each having a driving end which can be received in a bore in the end of a twist-drivable pin, and an opposite end at which torque can be applied. The cross-sectional shape of each of the drivers at its driving end has a first plurality of apexes whose relative locations coincide with the apexes of a regular polygon such as a hexagon. The drivers differ from one another in their cross-sectional shapes at the driving end by virtue of one or more faces of at least one of the drivers between adjacent pairs of apexes having a groove formed in it. Each of first and second twist-drivable pins has a bore extending into it which is defined by a second plurality of apexes arranged as a regular polygon such as a hexagon and which is open at one end.

8 Claims, 4 Drawing Sheets

(51) Int. Cl.
*F16B 23/00* (2006.01)
*A61B 17/88* (2006.01)
*A61B 90/90* (2016.01)

(52) U.S. Cl.
CPC ........ *F16B 23/003* (2013.01); *A61B 17/8877* (2013.01); *A61B 90/90* (2016.02); *B25B 15/005* (2013.01); *B25B 15/007* (2013.01); *B25B 15/008* (2013.01); *F16B 23/0038* (2013.01)

(58) Field of Classification Search
CPC ... B25B 15/005; B25B 15/007; B25B 15/008; B25B 15/001; F16B 23/003; F16B 23/0038
USPC ........ 606/304, 311, 232, 319; 411/403, 410; 81/436, 460, 461
See application file for complete search history.

(56) References Cited

U.S. PATENT DOCUMENTS

| | | | |
|---|---|---|---|
| 5,364,400 A | 11/1994 | Rego, Jr. | |
| 5,891,146 A | 4/1999 | Simon | |
| 6,045,554 A | 4/2000 | Grooms et al. | |
| 6,367,358 B1 | 4/2002 | Stacy | |
| 6,368,322 B1* | 4/2002 | Luks | A61B 17/861 606/308 |
| 6,663,656 B2* | 12/2003 | Schmieding | A61B 17/8615 606/232 |
| 6,843,729 B2* | 1/2005 | Hughes | B25B 15/005 470/11 |
| 6,988,432 B2* | 1/2006 | Brooks | F16B 23/0038 81/439 |
| 7,225,710 B2 | 6/2007 | Pacheco, Jr. | |
| 7,581,910 B2 | 9/2009 | Nebl | |
| 7,670,362 B2 | 3/2010 | Zergiebel | |
| 7,846,167 B2 | 12/2010 | Garcia et al. | |
| 8,291,795 B2 | 10/2012 | Hughes | |
| 8,459,155 B2 | 6/2013 | Canizares, Jr. | |
| 8,784,023 B2 | 7/2014 | Kuntner | |
| 2006/0266168 A1 | 11/2006 | Pacheco, Jr. | |
| 2012/0057949 A1 | 3/2012 | Canizares, Jr. | |
| 2012/0137842 A1 | 6/2012 | Guo | |
| 2012/0165107 A1 | 6/2012 | Guo | |
| 2013/0011216 A1* | 1/2013 | Frank | F16B 23/003 411/403 |

FOREIGN PATENT DOCUMENTS

| | | |
|---|---|---|
| CN | 2462131 Y | 11/2001 |
| CN | 101498333 A | 8/2009 |
| CN | 201851456 U | 6/2011 |
| CN | 201851459 U | 6/2011 |
| CN | 201874949 U | 6/2011 |
| CN | 201963679 U | 9/2011 |
| CN | 102562755 A | 7/2012 |
| CN | 202301363 U | 7/2012 |
| CN | 202348896 U | 7/2012 |
| CN | 202484047 U | 10/2012 |
| CN | 202579538 U | 12/2012 |
| EP | 2278175 A2 | 1/2011 |
| FR | 1585454 A | 1/1970 |
| GB | 2153033 A | 8/1985 |
| JP | 1-111811 J | 7/1989 |

OTHER PUBLICATIONS

Japanese Search Report for Corresponding Japanese App. No. 2015-548056, dated Oct. 17, 2017, 4 Pages.
Chinese Search Report for Chinese Application No. 201380066032.5, dated Nov. 16, 2016, 4 Pages.
PCT Written Opinion Regarding International Application No. PCT/US2013/075724, dated Jun. 23, 2015, 9 Pages.

* cited by examiner

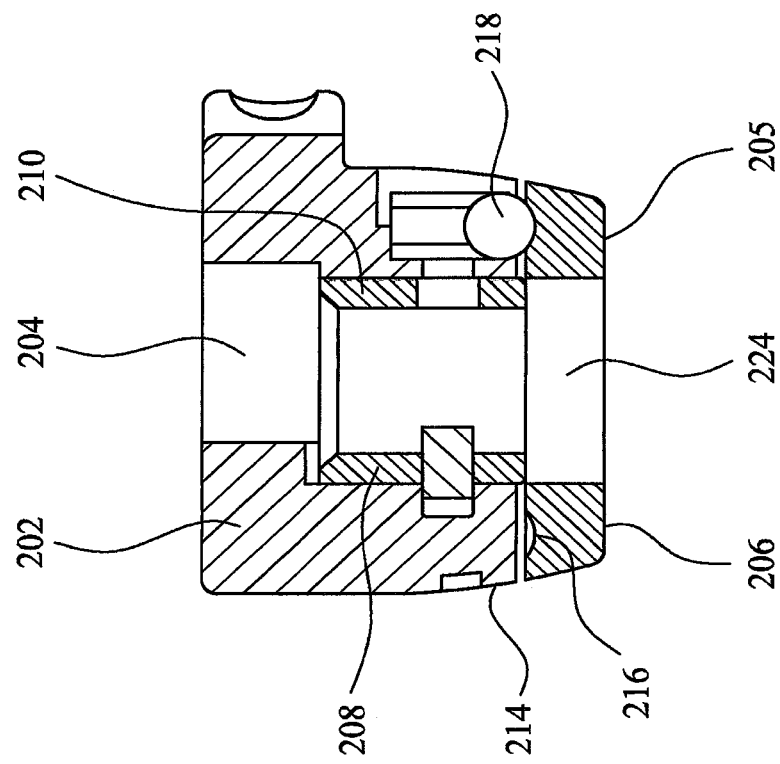
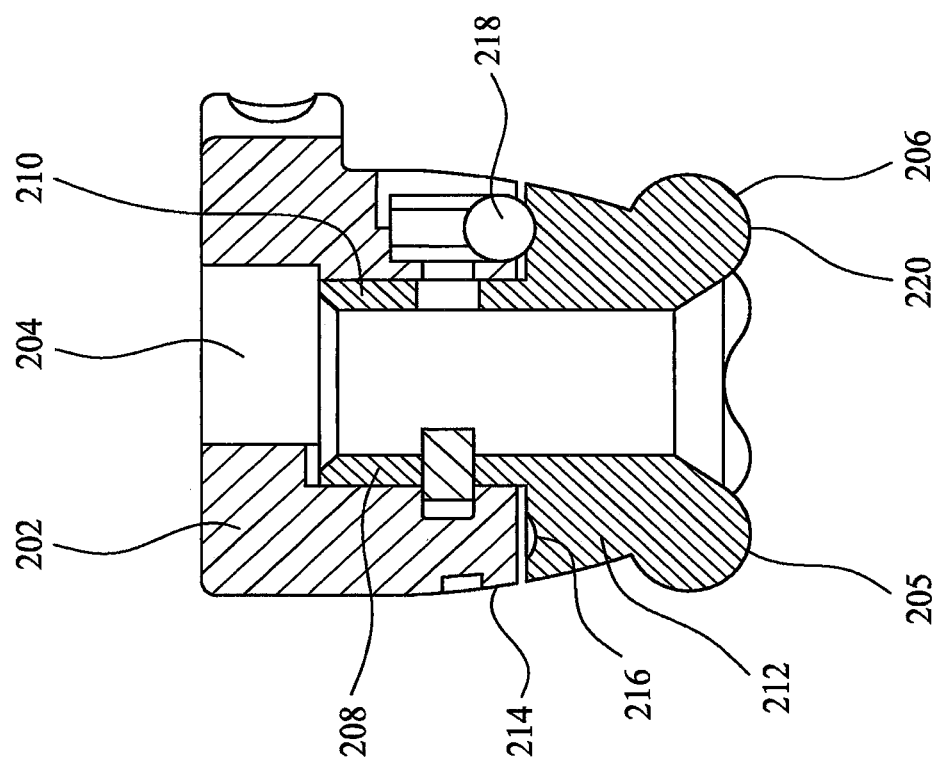
FIG. 7a
FIG. 7b

TWIST-DRIVABLE PIN ASSEMBLY

This application is a continuation under 35 U.S.C. § 120 of U.S. patent application Ser. No. 14/442,534 filed May 13, 2015, which is a National Stage 35 U.S.C. § 371 of International Patent Application Serial No. PCT/US2013/075724 filed Dec. 17, 2013, which claims priority to United Kingdom Patent Application GB1222688.2 filed Dec. 17, 2012, now abandoned. The entireties of each of those applications are incorporated herein by reference.

BACKGROUND OF THE INVENTION

This invention relates to a twist-drivable pin assembly which includes pins having a recess at one end in which the end of a driver can be received to twist the pin. The pin can be a fastener. The pin can be a shaft component of an instrument or other device.

It will often be preferred for the recess in the end of a pin in which the end of a driver is received to be shaped so that the end of a driver is a snug fit in the recess. Commonly used examples include a slot in the end of a fastener such as a screw which receives the flat blade of a driver tool, and a cross-shaped slot which receives the cross-shaped end of a driver tool.

The use of a driver tool whose end is hexagonal and received in a hexagonal recess (or bore) in a pin has the advantage that the multiple apexes provide for efficient torque transmission from the tool to the pin. Furthermore, the tool can be received more securely in the recess than is sometimes the case with screws are driven in by a flat blade or cross-shaped blade screwdriver. This means that the likelihood of damage to the substrate caused by the end of the driver if it becomes separated from the pin is reduced.

It can be desirable to differentiate between drivers which are used to impart a twist drive to respective pins, for example to respective fasteners drive them into a substrate, in particular to facilitate selection of a driver which is appropriate for use with a particular pin. Such drivers might differ from one another in terms of, for example, their sizes. For example, when the drivers have a driving end which is polygonal, for example hexagonal, the transverse dimension of one driver (measured between a line joining a first pair of adjacent apexes and a line joining a second pair of adjacent apexes opposite to the first pair when the number of apexes is even) might be different from the transverse dimension of another driver, and intended to be used with pins having polygonal bores with different transverse dimensions. Whether or not they differ in size, drivers might differ from one another in terms of other features such as, for example, limiting torque settings.

BRIEF SUMMARY OF THE INVENTION

The present invention provides a twist-drivable pin assembly in which driver bits each have a cross-sectional shape at their driving ends defined by a plurality of regularly arranged apexes, the cross-sectional shapes differing from one another by virtue of one or more faces of at least one of the drivers between adjacent pairs of apexes having a groove formed in it, and twist-drivable pins have markings associated with the open end of a polygonal driver bore whose shapes correspond to the cross-sectional shapes of the drivers which are intended to drive the pins.

Accordingly the invention provides a twist-drivable pin assembly comprising:

a. first and second drivers, each of which has a driving end which can be received in a bore in the end of a twist-drivable pin, and an opposite end at which torque can be applied, the cross-sectional shape of each of the drivers at its driving end having a first plurality of apexes whose relative locations coincide with the apexes of a regular polygon, the drivers differing from one another in their cross-sectional shapes at the driving end by virtue of one or more faces of at least one of the drivers between adjacent pairs of apexes having a groove formed in it, b. first and second twist-drivable pins, each having a bore extending into it which is defined by a second plurality of apexes arranged as a regular polygon and which is open at one end, in which at least one of the drivers can be received, the number of apexes of the second plurality being equal to the number of apexes of the first plurality, the first and second pins differing from one another by virtue of markings associated with the open end of the polygonal bore of at least one of the first and second pins, in which the shape defined by the markings corresponds to the cross-sectional shape of a corresponding one of the first and second drivers.

The twist-drivable pin assembly of the invention has the advantage that a user is able to use the markings on the twist-drivable pins to provide a visual indication as to the driver which is to be used to twist-drive a selected pin. The reverse is also true. The invention uses graphical indications in the form of shapes in order to identify corresponding twist-drivable pins and drivers. In particular, the shape is embodied in the cross-section of the driver. This has the advantage of being easy for a user to recognise. The cross-sectional shape of the driver can be recognised from a number of different angles: the shape can of course be recognised when the driver is viewed end on from a position in line with its axis, but it can also be recognised when the driver is viewed from one side. It can be preferred that the grooves formed in one or each of the drivers, by which the drivers differ from one another, extend to the driving end of the driver. This facilitates recognition of the cross-sectional shapes of the drivers because the cross-sectional shapes correspond to the shapes of the end faces of the drivers. The cross-sectional shape can therefore be seen in a view of the driver which includes the end face (which might be an oblique view). The identification of a driver or a pin can then be communicated orally by describing its shape. For example, a driver might be described as "the hex driver" or "the star driver". This can be an important advantage in circumstances in which a user has an assistant who he relies on to pass tools (or instruments) or pins (for example fasteners) to him, for example in an operating theatre when a surgeon requests an assistant to pass tools or pins to him.

The groove or grooves can be formed in the driver when the driving end of the basic polygonal configuration of the driver is created, for example by casting or pressing or stamping or cutting. The groove or grooves can be formed in a driver in a step which is performed after the basic polygonal configuration of the driver is created, for example by a step in which a groove is cut into a face of the driver.

It will generally be preferred for the number of apexes at the driving ends of the drivers to be six. The bores in the pins would then generally also have six apexes. Such drivers in the twist-drivable pin assembly of the invention have a hexagonal array of six apexes so that the driving ends of the drivers can be received in hexagonal bores in pins to impart torque to the pins. This means that, while the shape coding of the drivers corresponds to the shape markings on the pins to help a user to select an especially appropriate driver to import torque to a pin, the pin can be driven into the substrate or removed from the substrate using a polygonal driver whose cross-sectional shape is that of a regular hexagon.

The driving ends of the drivers might have a number of apexes other than six. The example, the number of apexes defined by the driving ends of the drivers might be three, or four, or five, or seven or eight. Preferably the number of apexes is at least four. Preferably the number of apexes is not more than ten, especially not more than eight. It can be preferred for some applications that the number of apexes is even.

The twist-drivable pins can be fasteners. The fasteners will frequently be screws and will have an external thread. The design of the thread will depend on the application in which the screw is being used. The screw might be intended to fasten an orthopaedic implant to a bone. The screw can then have a thread which is characteristic of a bone screw. The screw might be used to fasten two metallic components together where one of the components has an internal thread. The thread on the screw might then be such as is characteristic of a machine screw. Such threads are known. The length of a fastener will be selected according to the application in which it is going to be used, as with existing conventional fasteners. Other threaded fasteners might be used, for example with an internal thread in the form of a nut.

The fastener might be a bayonet fastener.

The fasteners which are included in the assembly of the invention can be used in a range of applications. These applications might include, for example, engineering, construction, handicraft, and so on. The fasteners can be used in surgical applications, especially in applications in orthopaedic surgery. For example, fasteners can be used to fix components of joint prostheses in place. They can be used to fix implants for treatment of broken of bones. Such implants might include bone plates which are fitted directly or indirectly on the external surface of a bone, and pins and nails which are fitted in the intramedullary cavity within a bone. It is an advantage of the present invention that fasteners can be removed using a plain polygonal driver (for example a hexagonal driver) instead of a driver which has one or more grooves provided in one or more faces. This avoids the need to locate a driver whose driver head has a particular cross-section shape, which might not be available if a fastener has to be removed after lapse of a considerable period of time since a component was implanted in a patient. It will therefore be understood that the features of the cross-sectional shape of the driver and the shaped marking features on the fasteners or other twist-drivable pin serve to identify a driver to drive a pin having a plain polygonal bore, but do not preclude the use of a driver whose driving end has the cross-sectional shape of a plain polygon to drive the pin.

A twist-drivable pin which is used in the assembly of the invention can be a shaft component of an instrument or device. The shaft can have a bore formed in it at one end in which the driving end of a driver can be received to cause the shaft to rotate. The shaft can be rotated to adjust the instrument or device. For example, rotation of the shaft might cause the tension on a component of the instrument or device to change. Rotation of the shaft might cause a latch to be opened or to be closed. Rotation of the shaft might cause another component of the instrument or device to move, in rotational or in translation. Such movement might involve interengaging gears, or a rack and pinion assembly. The instrument or device might be a measuring instrument.

It is known for a twist-drivable shaft in such an instrument to have a knob which can be gripped by a user to cause the shaft to rotate. The present invention provides control over rotation of the shaft so that it is not rotated unless an appropriately compatible driver is used. The length of a pin in the form of shaft component of an instrument of device will depend on the function of the shaft component. The shaft component should have an appropriate length to enable it to perform its intended function. Frequently, the shaft component will be fixed in place in a housing of the instrument or device of which it forms a part, such that it can be rotated in the housing but will not in normal operation (apart from for example disassembly for cleaning) be separated from the housing. Techniques for fixing the shaft component in place so that it can be rotated are well known, and might include for example a circlip or a grub screw engaging a groove which extends at least part of the way around the circumference of the shaft component.

An instrument or device which includes a twist-drivable shaft component can be an instrument which is used in surgery. For example it can be suitable for use in orthopaedic surgery. The instrument can be used to make a measurement, for example of the size of a bone or of the spacing between two bones, to identify the appropriate size of an implant component which should be used to suit a patient's anatomy. The instrument can be used to prepare a bone to receive an implant component.

The invention also provides a kit for use in surgery, which includes an orthopaedic implant having at least one bore formed in it for receiving a fastener, and a twist-drivable pin assembly according to the invention, especially in which the fastener is a pin such as a screw or other twist-drivable fastener.

The driving end of a driver in the assembly of the invention can have a groove in one face. It can have grooves formed in more than one face. Different combinations of arrangements of grooves produce drivers which have different shapes, enabling the drivers to be distinguished from one another. The groove should preferably extend to the end of the driver which is inserted into the bore in a pin. This means that the cross-sectional shape of the driver can be identified by looking at the end of the driver along the axis of the driver.

Optionally, the length of the or each groove is at least about 3 mm, or at least about 4 mm, or at least about 5 mm. Optionally, the ratio of the length of the groove to the transverse dimension of the hexagonal driving end (measured between straight lines joining opposite pairs of apexes) is at least about 1.0, or at least about 1.2, or at least about 1.5. A longer groove can facilitate identification of the driver.

Optionally, the depth of the or each groove is at least about 1 mm, or at least about 2 mm, or at least about 5 mm. Optionally, the ratio of the depth of the groove to the transverse dimension of the polygonal, for example hexagonal, driving end (measured between straight lines joining opposite pairs of apexes when the number of apexes is even) is at least about 0.05, or at least about 0.1, or at least about 0.15. A deeper groove can facilitate identification of the driver. Optionally, the ratio of the depth of the groove to the transverse dimension of the polygonal driving end is not more than about 0.25, or not more than about 0.2.

When the driver has six faces and grooves are provided in each of the six faces between adjacent apexes, the driver will have the appearance when viewed in cross-section of a six pointed star. Such a driver can be similar to drivers which are commercially available, sold under the trade mark Torx.

When the driver has six faces and the number of faces of the driver in which grooves are provided is 2, 3 or 4, the driver can be designed with different arrangements of the grooves. For example, when the number of grooved faces is two, the grooved faces can be arranged adjacent to one another (1,2 positions), or separated by one or two faces (1,3 and 1,4 positions, respectively). When the number of grooved faces is four, the faces which are not grooved can be arranged adjacent to one another (1,2 positions), or separated by one or two faces (1,3 and 1,4 positions, respectively).

When the driver has six faces and the number of faces of the driver in which grooves are provided is three, the grooved faces can be alternate faces (1,3,5 positions) so that adjacent grooves subtend an angle of 120° at the axis of the driver.

It can be preferred to provide grooves in two faces or three faces of a driver with six faces because the grooved faces can be arranged so that they are uniformly spaced around the axis of the driver. This can provide an appearance which is easily recognised.

It is to be noted that the number and arrangement of grooved faces around the axis of a driver do not by themselves affect the ability of a driver to fit into a bore in twist-drivable pin, so that two drivers which differ only in respect of the number and arrangement of grooved faces might be used interchangeably in a selected pin. The grooves in the faces of the driver should be such that the ability of the apexes to engage and to deliver an applied torque to the apexes which define the bore in the pin is not compromised to a degree which means that the driver is unable to impart a desired torque to the pin, for example to drive a screw fastener into a substrate.

The markings on one or each of the first and second pins can be provided by recesses below the surface of the pin surrounding the open end of the bore. Such recesses can be formed during manufacture of the pin, for example as part of a process of forming the bore in the pin. The recesses might therefore be formed by processes such as cutting, stamping, pressing, and milling. Markings which are provided by recesses below the surface of the pin have the advantage that they are better able to be identified by a user, even in conditions of poor light or when the pin is in an environment in which fluids are present. In addition, a marking provided by a recess below the surface of the pin can contribute to an appearance that the bore in the pin has a cross-sectional shape which corresponds to that of the recess (when the cross-sectional shape of the bore is actually polygonal, for example hexagonal). This can help a user in the process of selecting a driver for the pin.

The markings on one or each of the first and second twist-drivable pins can be formed by removing material from the surface of the pin surrounding the open end of the bore after the bore has been formed. This can be preferred because it can allow pins to be differentiated in small batches. Techniques which can be used to form the markings can include, for example engraving and etching. Engraving can be performed using a cutting tool. Engraving can be performed using a laser. Etching can be performed using appropriate etching materials. The selection of a removal technique will depend on factors which include the material of the pin and the shape and depth of the markings which are to be created on the pin.

The twist-drivable pin will frequently be formed from a metal (although other materials might be used such as polymeric and ceramic materials). Metals which are commonly used to make twist-drivable fasteners or other pins are well known. Examples of suitable materials for a fastener which is intended for use in a surgical procedure, such as an orthopaedic procedure, include certain stainless steels and titanium its alloys.

It can be preferred that the depth of the markings below the surface of the twist-drivable pin surrounding the bore is at least about 0.2 mm, for example at least about 0.3 mm, or at least about 0.5 mm, or at least about 0.7 mm, or at least about 1.0 mm. The markings should be sufficiently deep so that they can be observed clearly by a user. They can also create a visual impression that the shape of the bore in the twist-drivable pin for receiving the driver corresponds to the shape defined by the markings. The markings can have a non-uniform depth so that they appear textured. This can enhance the contrast between the markings and surrounding areas of the surface of the twist-drivable pin. The depth of a marking which is defined by a textured area can be small because of the enhanced contrast provided by the texturing. The contrast between the markings and surrounding areas of the surface of the twist-drivable pin can be enhanced by the introduction of a dye or other contrast medium in the area of the markings. This might be done when the markings are formed, for example as part of a laser marking or an etching process.

It can be preferred that the depth of the markings below the surface of the twist-drivable pin surrounding the bore is not more than about 5.0 mm, for example not more than about 3.5 mm, or not more than about 2.0 mm. The depth of the markings might be not more than about 1.0 mm for some applications. Shallow markings can be appropriate when the size of the twist-drivable pin is small. It can be preferred for the depth of the markings to be shorter than the depth of the bore in the pin so that a person inspecting the pin is able to recognise that the bore in the pin in which the driver is received to apply torque to the pin is polygonal. This can be important when, for example, a fastener is to be removed from a substrate. This might be after the passage of a considerable period of time following initial use of the fastener. For example, when the fastener is being used in a surgical application, especially in orthopaedic surgery (for example to fasten an implant such as a bone plate to a patient's bone), a surgeon might have to remove the fastener some time after the initial implantation. This might be for example after the passage of several months or several years. It might be at the end of the treatment for the initial condition for which the fastener was deployed. It might be as part of the continuation of the initial treatment. It might be to allow another condition to be treated. It can be desirable that the surgeon should be able to recognise that the driver that is appropriate for removal of the fastener is one which has a polygonal, especially hexagonal, cross-section, notwithstanding the markings which might be visible on the fastener.

The markings are provided on the twist-drivable pin in areas surrounding the open end of the polygonal bore which lie radially outside of the straight lines joining adjacent apexes of the bore.

The shapes of the markings on the twist-drivable pins and the corresponding cross-sectional shapes of the drivers can be used to differentiate between different sizes of components of the assembly. For example, fasteners or other twist-drivable pins might have similar but different sizes of bore. In a particular example, a first pin might have a hexagonal bore size 6 mm (measured between opposite faces) and a second pin might have a hexagonal bore size 6.5 mm. It can be difficult to identify the size of a pin from a visual inspection of the bore when the bores of pins in the assembly have similar sizes, and similarly to identify the size of a driver from a visual inspection of the driving end. The creation of a distinctive cross-section shape on the driving end by provision of grooves in faces of the driving end, and the provision of corresponding markings on the pin, can help to differentiate the sizes.

The shapes of the markings on the twist-drivable pins and the corresponding cross-sectional shapes of the drivers can be used to differentiate between different lengths of pins.

Optionally, the transverse dimension of the polygonal driving end of the first driver (measured between a line joining a first pair of adjacent apexes and a line joining a second pair of adjacent apexes opposite to the first pair if the number of apexes is even, or between a first apex and a line joining a pair of adjacent apexes opposite to the first apex if the number of apexes is odd) is different from the transverse dimension of the polygonal driving end of the second driver.

Generally, the transverse dimension of the polygonal bore in the twist-drivable pins (measured between a line joining a first pair of adjacent apexes and a line joining a second pair of adjacent apexes opposite to the first pair if the number of apexes is even, or between a first apex and a line joining a pair of adjacent apexes opposite to the first apex if the number of apexes is odd) is at least about 1.0 mm, optionally at least about 1.5 mm, or at least about 2.0 mm. The benefits of the invention in terms of visual recognition of characteristic shapes are reduced at smaller sizes.

The shapes of the markings on the twist-drivable pins and the corresponding cross-sectional shapes of the drivers can be used to differentiate between pins which can withstand application of different maximum torques.

The shapes of the markings on the twist-drivable pins can be used to differentiate between different drivers which are to be used in a particular procedure. For example, it might be that the driver that is to be used in one step of a procedure has a first design, and a driver that is to be used in another step of a procedure has a second design. The designs might differ from one another in any of a number of features, for example handle configuration, drive mechanism and so on. The marking on a pin can help the user to identify the driver which is suitable for use to impart torque to that pin.

The assembly of the invention might include more than two drivers where the drivers can be differentiated from one another by different arrangements of grooves in the polygonal faces. The assembly can then include more than two pin which can be differentiated from one another by different markings associated with the open ends of the bores in the pins.

The drivers in the assembly of the invention might be driver bits which are used with another driver component which can be used to apply torque to a selected driver bit. For example, the driver bits might be used with a driver handle. A suitable construction of handle might be one which has a socket for receiving the end of a driver bit which is opposite to the driving end of the bit. The handle might include a mechanism for indicating that a selected torque value has been applied to the pin. The handle might include a ratchet mechanism allowing the handle to be turned through a limited angle back and forth, with torque being applied to the pin when the handle is turned in only one of the directions.

Driver bits might be used with a powered driver.

BRIEF DESCRIPTION OF THE DRAWINGS

Embodiments of the invention are described below by way of example with reference to the accompanying drawings, in which:

FIGS. 7a and 7b are sectional elevations through the mechanisms shown in FIGS. 6a and 6b.

DETAILED DESCRIPTION OF THE INVENTION

Figure 1:
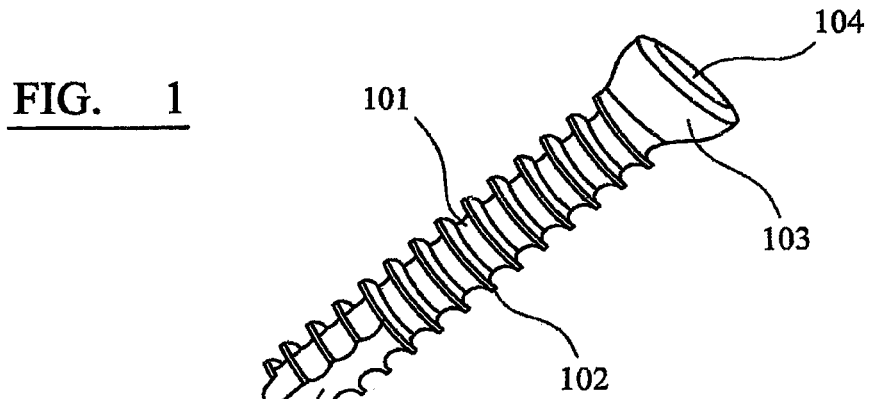
FIG. 1 is an isometric view of a bone screw.

Referring to the drawings, FIG. 1 shows a bone screw which includes a shank 101 having a thread 102 formed on it. The screw has an enlarged head 103 which has a bore 104 extending into it. The bore has a hexagonal shape when viewed along the axis of the screw. The screw has a cutting tip 105.

The hexagonal bore in the screw can receive the hexagonal end of a driver tool which can be used to apply torque to the screw to drive it into a bone. An example of an application for the screw is to fasten a bone plate to a bone.

Figure 2A:
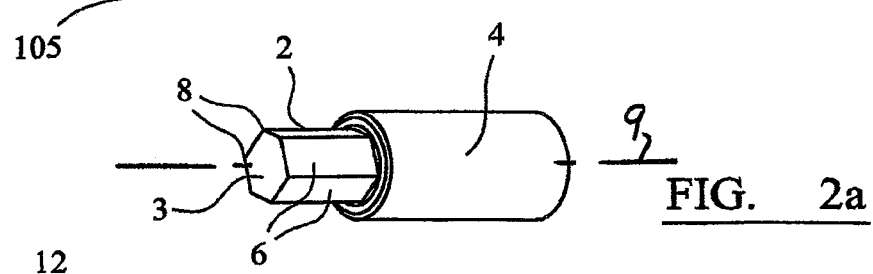
FIGS. 2a, 2b and 2c are isometric views of the driving ends of three driver tools in which the driving ends have different cross-sectional shapes.
Figure 3A:
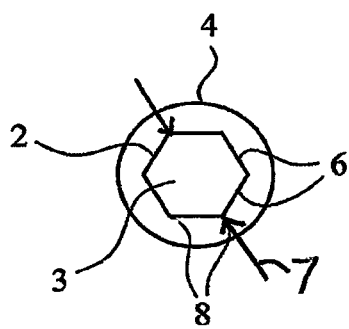
FIGS. 3a, 3b and 3c are end views of the driving ends of the three driver tools shown in FIGS. 2a, 2b and 2c, respectively.

FIGS. 2a and 3a are end and isometric views of the driving end 2, including its end face 3, of a driver tool. The driving end is provided at the end of a shaft 4. The driver tool can include a handle (not shown) which the shaft is fastened to. The shaft can be fastened rigidly to the handle. The tool can include a ratchet mechanism which ensures that the shaft rotates with the handle when the handle is rotated in one direction and that the handle can rotate independent of the shaft in the other direction. The handle can include a socket for receiving the shaft. The socket can be capable of receiving different shafts interchangeably.

The cross-sectional shape of the driving end 2 of the driving tool, and the shape of its end face 3, are that of a regular hexagon with six flat faces 6 separated by six apexes 8, with the internal angle between adjacent apexes being 120°.

Figure 2B:
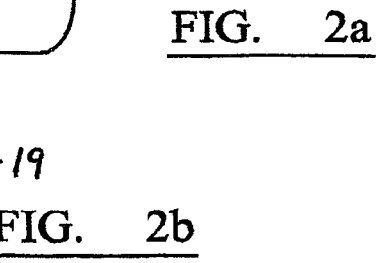
Figure 3B:
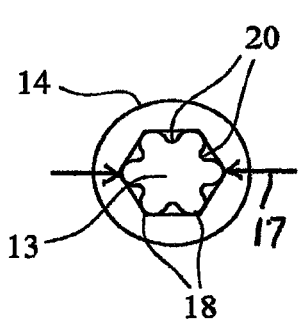

FIGS. 2b and 3b are end and isometric views of the driving end 12, including its end face 13, of a driver tool. The driving end is provided at the end of a shaft 14. The cross-sectional shape of the driving end has six apexes 18 whose relative locations coincide with the apexes of a regular hexagon. Grooves 20 are provided in each of the six faces of the driving end between adjacent pairs of the apexes. The grooves extend to the end face 13 of the driving tool. The cross-sectional shape of the driving end, which is the same as the shape of the end face 13, is that of a six pointed star, and is similar to the shapes of drivers which are commercially available, sold under the trade mark Torx.

The grooves in the side faces of the driving end are formed by a machining operation performed on the flat faces of a driver having a hexagonal cross-section shape, as shown in FIG. 2a. The configuration of the grooves is such that all of the apexes of the hexagon are unaffected by the machining step.

Figure 2C:
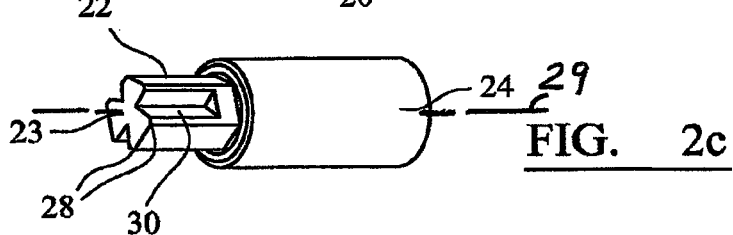
Figure 3C:
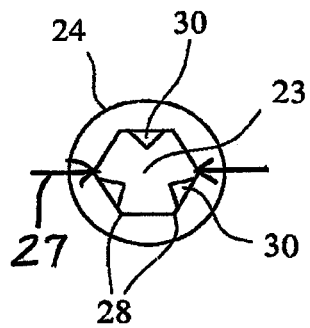

FIGS. 2c and 3c are end and isometric views of the driving end 22, including its end face 23, of a driver tool. The driving end is provided at the end of a shaft 24. The cross-sectional shape of the driving end has six apexes 28 whose relative locations coincide with the apexes of a regular hexagon. Grooves 30 are provided in three of the six faces 26 of the driving end between adjacent pairs of the apexes. Adjacent grooved faces are separated by a face which is not grooved so that the grooves are formed in the "1,3,5" faces of the hexagon. The grooves extend to the end face 23 of the driving tool. The cross-sectional shape of the driving end, which is the same as the shape of the end face 23, can be seen to have three lobes, and to be similar to that of a three-leaved shamrock.

Figure 4A:
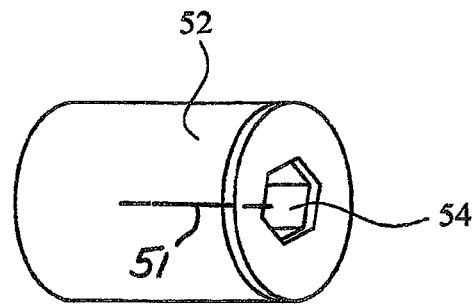
FIGS. 4a, 4b and 4c are schematic isometric views of the heads of three fasteners having markings associated with the open ends of hexagonal bores in which driver bits can be received.
Figure 4B:
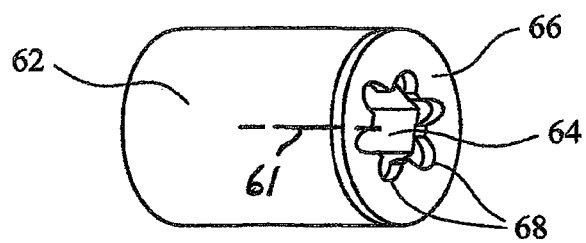
Figure 4C:
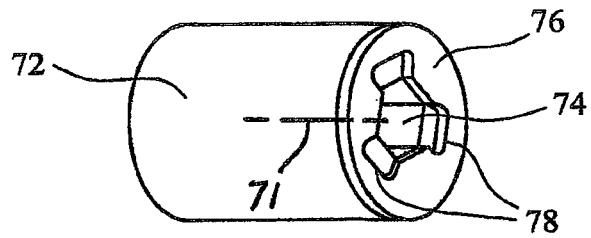

It will be understood that the shape of the head of the screw will not in practice be as shown in FIGS. 4a to 4c. For example, the head of a screw might have the general shape shown in FIG. 1. The representations of the screw heads in FIGS. 4a to 4c are included to provide information to the reader regarding features of the bore and associated marking features of a screw head which can be used in the assembly of the invention.

Figure 5A:
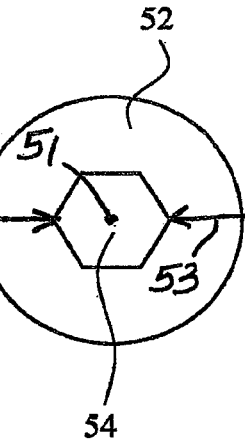
FIGS. 5a, 5b and 5c are end views of the driving ends of the three driver tools shown in FIGS. 4a, 4b and 4c, respectively.

FIGS. 4a and 5a shows schematically the head 52 of a screw or other fastener which can be driven by the driver shown in FIG. 2a. The head has a bore 54 extending into it which is open at the end surface of the fastener. The bore is defined by six apexes which are arranged as a regular hexagon. The size of the bore is such that the driving end 2 of the driver shown in FIG. 2a is a snug sliding fit in the bore.

Figure 5B:
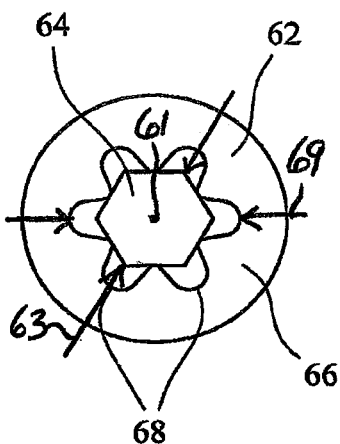

FIGS. 4b and 5b shows schematically the head 62 of a screw or other fastener which can be driven by the driver shown in FIG. 2b. The head has a bore 64 extending into it which is open at the end face 66 of the fastener. The bore is defined by six apexes which are arranged as a regular hexagon. The size of the bore is such that the driving end 12 of the driver shown in FIG. 2b is a snug sliding fit in the bore. The bore can also receive the driving end of a driver whose cross-sectional shape is hexagonal without grooves in any of its faces (as shown in FIG. 2a), in which the distance between opposite faces of the hexagon is the same as the distance between a line joining a first pair of adjacent apexes and a line a second pair of adjacent apexes opposite to the first pair of the driving end 12.

The end face 66 of the fastener has a set of six curved segments 68 engraved in it, arranged around the end of the hexagonal bore in a hexagonal array. In the embodiment shown in FIG. 4b, each of the curved segments is centred on a respective apex of the hexagonal bore. However, they could be arranged differently relative to the bore, for example with each of the curved segments centred on a respective face of the hexagonal bore. The curved segments are formed by a machine engraving step. Opposite faces of the hexagonal bore are 4 mm apart. The depth of the curved segments cut into the end face of the fastener is about 0.7 mm. The arrangement of the curved segments around the hexagonal bore creates a star-shaped marking on the end face, similar in appearance to the shape of the end face 13 of the driver shown in FIG. 2b. It will be understood that the size of the star-shaped marking will be larger than the size of the star-shaped end face of the driver.

Figure 5C:
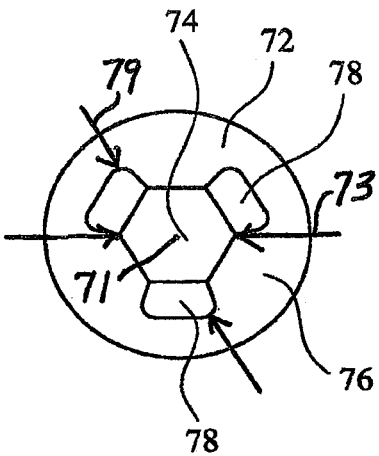

FIGS. 4c and 5c shows schematically the head 72 of a screw or other fastener which can be driven by the driver shown in FIG. 2a. The head has a bore 74 extending into it which is open at the end face 76 of the fastener. The bore is defined by six apexes which are arranged as a regular hexagon. The size of the bore is such that the driving end 12 of the driver shown in FIG. 2c is a snug sliding fit in the bore. The bore can also receive the driving end of a driver whose cross-sectional shape is hexagonal without grooves in any of its faces (as shown in FIG. 2a), in which the distance between opposite faces of the hexagon is the same as the distance between a line joining a first pair of adjacent apexes and a line a second pair of adjacent apexes opposite to the first pair of the driving end 12.

The end face 76 of the fastener has a set of three rectangular segments 78 engraved in it, located on alternate edges (edges "1,3,5") of the hexagonal bore 74. The rectangular segments are formed by a machine engraving step. Opposite faces of the hexagonal bore are 4 mm apart. The depth of the rectangular segments cut into the end face of the fastener is about 0.7 mm. The arrangement of the rectangular segments around the hexagonal bore creates a three lobe shaped marking on the end face, similar in appearance to the shape of the end face 23 of the driver shown in FIG. 2c. It will be understood that the size of the three lobe-shaped marking will be larger than the size of the three lobe-shaped end face of the driver.

The fasteners shown in FIGS. 4a to 4c can differ from one another in one or more respects, for example in the transverse sizes of the hexagonal bores, lengths, torque ratings, intended uses and so on. The engraved markings on the end faces of the fasteners shown in FIGS. 4b and 4c create the impression of shaped bores where the shapes correspond to the shapes of the end faces of the drivers shown in FIGS. 2b and 2c. The eye of a user is drawn to the bores in the fasteners when identifying an appropriate driver so that the association of the marking with the bore means that the marking registers in the mind of the user of the assembly. The user is able to identify drivers having cross-sections whose shapes correspond to the shapes of the markings by inspection of the shapes of the end faces of the drivers.

FIGS. 6 and 7 show a twistable adjuster which can be incorporated into an instrument. The adjuster has a housing 202 with a bore 204 extending through it. A shaft 205 is mounted in the housing. The shaft can be rotated in the housing. The top end 206 of the shaft protrudes from the housing. The opposite bottom end 208 of the shaft is accessible within the housing through the bore 204. The shaft can be connected to another component of the instrument at its bottom end.

The shaft can be rotated in the housing to impart movement to the other component to which it is connected.

The shaft has cylindrical portion 210 at the bottom end which fits in the bore in the housing so that the shaft can rotate in the housing. The shaft has a protruding portion 212 at its top end which faces an outwardly facing surface 214 of the housing. The face of the protruding portion which faces the housing has a plurality of shallow recesses 216 formed in it. The face of the housing which faces the protruding portion 212 of the shaft has a spring loaded ball bearing 218 mounted in a shallow bore. The ball bearing is urged into successive ones of the shallow recesses in the protruding portion of the shaft as the shaft is rotated. In this way, the rotation of the shaft in the housing is indexed with definite click stops provided by the ball bearing fitting into the recesses.

Figure 6A:
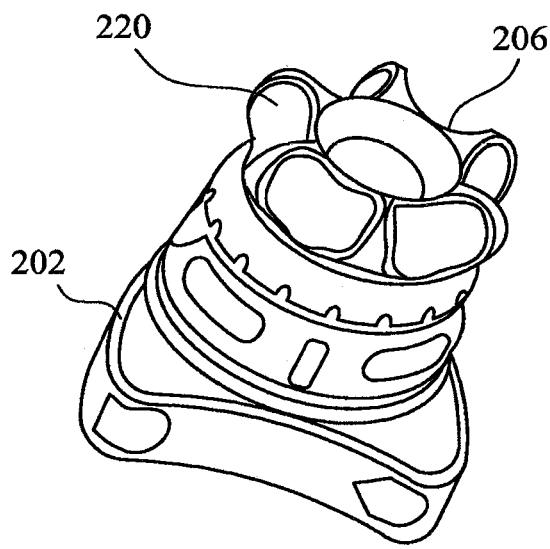
FIGS. 6a and 6b are isometric views of through twist adjustment mechanisms which can be incorporated into a surgical instrument, using a knob and using a twist-drivable pin in accordance with the invention, respectively
Figure 6B:
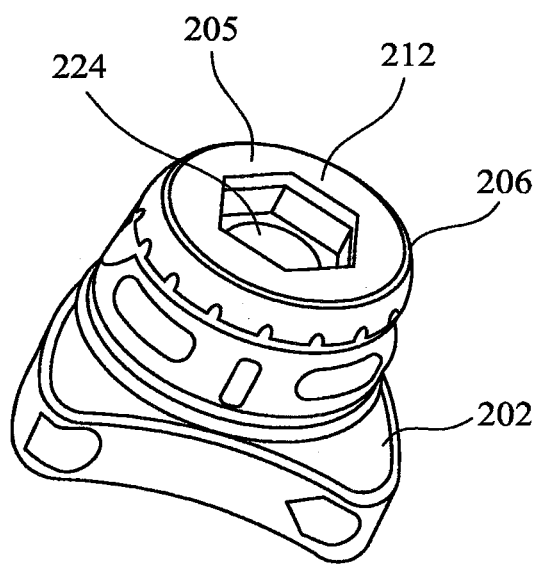

In the adjuster which is shown in FIGS. 6a and 7a, the protruding portion 212 of the shaft is formed as a multi-lobe cap 220 which can be gripped by a user to cause the shaft to rotate. In the adjuster according to the invention which is shown in FIGS. 6b and 7b, the protruding portion 212 of the shaft has a hexagonal bore 224 extending into it in which a driver can be received. In the particular adjuster shown in the drawings, the bore is a plain hexagonal bore.

Figure 8:
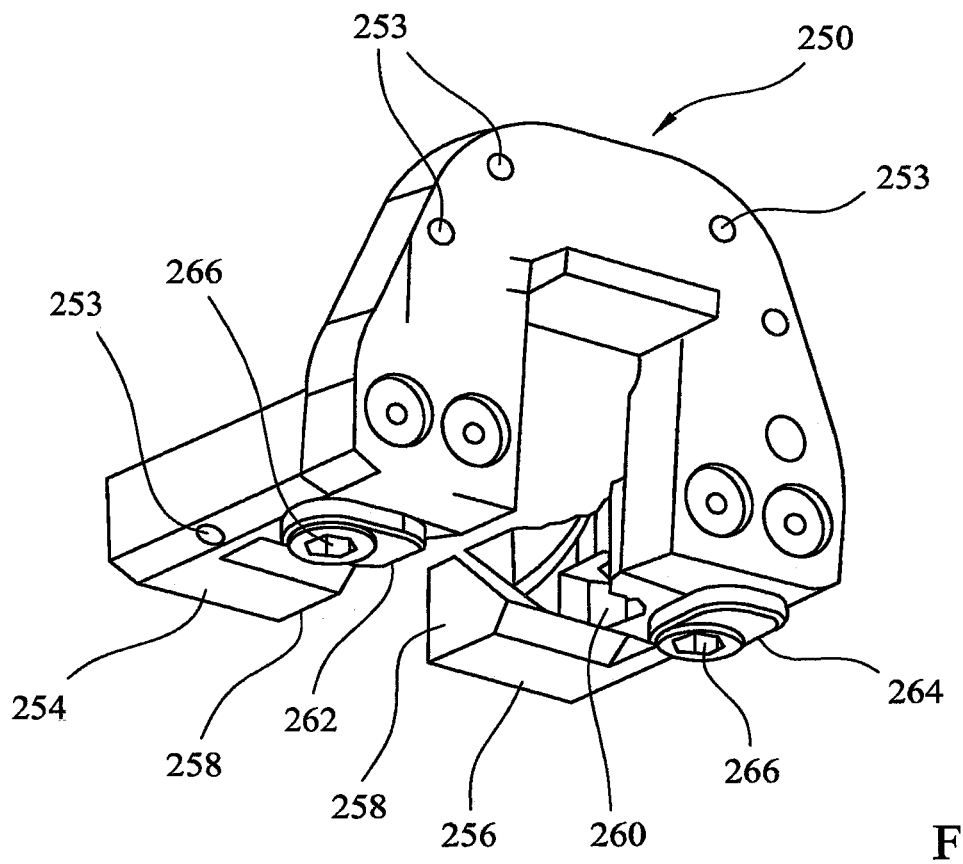
FIG. 8 is a prospective view of a cutting guide.

FIG. 8 shows a cutting guide 250 which has a pair of latches 252 for retaining another instrument in place. The cutting guide can be used to prepare the distal end of a femur to receive an implant component of a knee joint prosthesis. The cutting guide has holes 253 formed in it for receiving fixation pins in a conventional manner. The cutting guide as a pair of limbs 254, 256 which define edge surfaces 258 for guiding a cutting blade to form a notch in the femur. Each of the limbs has a shaped cavity 260 formed in it for engaging a correspondingly shaped protrusion on a cooperating mating instrument such as a reamer guide. The cutting guide as a pair of latches which can be rotated between latched and unlatched positions. A first one 262 of the latches is shown in the latched position and a second one 264 of the latches is shown in the unlatched position. The latches hold protrusions on a cooperating instrument in place in the shaped cavities 260 when in their latched positions. Each of the latches has a hexagonal bore 266 extending into it in which a driver can be received to rotate it between its latched and unlatched positions. In the particular adjuster shown in the drawings, the bore is a plain hexagonal bore.

The invention claimed is:

1. A surgical kit, comprising:
a plurality of pin drivers, each pin driver including a driving end, and
a plurality of twist-drivable pins including a first twist-drivable pin including an end surface, an opening defined in the end surface, and a plurality of inner faces extending inwardly from the opening to define a bore having a first cross-sectional shape of a regular polygon, wherein a first plurality of apexes join the inner faces,
wherein the plurality of pin drivers include a first pin driver including a driving end sized to be received the bore of the first twist-drivable pin and apply torque to the first twist-drivable pin, wherein the driving end includes a plurality of outer faces joined by a second plurality of apexes equal in number to the first plurality of apexes, and a groove is defined in at least one of the plurality of outer faces between an adjacent pair of apexes of the second plurality of apexes such that the driving end of the first pin driver has a second cross-sectional shape different the first cross-sectional shape, and
wherein the first twist-drivable pin includes a first visual marking on its end surface, the first visual marking having a shape that matches the second cross-sectional shape of the driving end of the first pin driver to provide a user with an indication that the first pin driver is configured for insertion into the bore of the first twist-drivable pin,
wherein the first visual marking of the first twist-drivable pin and the inner faces defining the bore of the first twist-drivable pin are sized and shaped such that the driving end of each pin driver configured for insertion into the bore of the first twist-drivable pin applies a force only to the inner faces of the bore of the first twist-drivable pin,
wherein the plurality of twist-drivable pins include a second twist-drivable pin including an end surface, an opening defined in the end surface, and a plurality of inner faces extending inwardly from the opening to define a bore having a third cross-sectional shape of a regular polygon, wherein a third plurality of apexes join the inner faces and the first cross-sectional shape of the bore of the first twist-drivable pin is the same as the third cross-sectional shape of the bore of the second twist-drivable pin,
wherein the plurality of pin drivers include a second pin driver including a driving end sized to be received the bore of the second twist-drivable pin, wherein the driving end of the second pin driver includes a plurality of outer faces joined by a fourth plurality of apexes equal in number to the third plurality of apexes, and the plurality of outer faces are devoid of any grooves between any adjacent pairs of apexes of the fourth plurality of apexes such that the second pin driver has a fourth cross-sectional shape, and
wherein the fourth cross-sectional shape is the same as the first cross-sectional shape such that the driving end of the second pin driver is configured for insertion into the bore of the first twist-drivable pin and applies a force to the inner faces of the bore of the first twist-drivable pin.

2. The surgical kit of claim 1, wherein the first visual marking is an engraved marking on the first twist-drivable pin.

3. The surgical kit of claim 2, wherein the first visual marking is a laser-engraved marking.

4. The surgical kit of claim 1, wherein the first visual marking extends a first distance into the first twist-drivable pin, and the bore of the first twist-drivable pin extends a second distance into the first twist-drivable pin greater than the first distance.

5. The surgical kit of claim 1, wherein the groove of the first pin driver is one of a plurality of grooves defined in the plurality of outer faces.

6. The surgical kit of claim 5, wherein each outer face of the plurality of outer faces has at least one groove of the plurality of grooves defined therein.

7. The surgical kit of claim 1, further comprising:
a third twist-drivable pin including an end surface, an opening defined in the end surface, and a plurality of inner faces extending inwardly from the opening to define a bore having a fifth cross-sectional shape of a regular polygon, wherein a fifth plurality of apexes join the inner faces, and
a third pin driver including a driving end sized to be received in the bore of the third twist-drivable pin and apply torque to the third twist-drivable pin, wherein the driving end includes a plurality of outer faces joined by a sixth plurality of apexes equal in number to the first plurality of apexes, and a groove is defined in at least one of the plurality of outer faces between an adjacent pair of apexes of the sixth plurality of apexes such that the driving end of the third pin driver has a sixth cross-sectional shape different the fifth cross-sectional shape,
wherein the third twist-drivable pin includes a second visual marking on its end surface, the second visual marking having a shape that matches the sixth cross-sectional shape of the driving end of the third pin drive to provide a user with an indication that the third pin driver is configured for insertion into the bore of the third twist-drivable pin,
wherein the second visual marking of the third twist-drivable pin and the inner faces defining the bore of the third twist-drivable pin are sized and shaped such that the driving end of each pin driver configured for insertion into the bore of the third twist-drivable pin applies a force only to the inner faces of the bore of the third twist-drivable pin, and wherein the sixth cross-sectional shape of the third pin driver is different from second cross-sectional shape of the first pin driver.

8. The surgical kit of claim 7, wherein the first cross-sectional shape of the first twist-drivable pin is the same as the third cross-sectional shape of the second twist-drivable pin and the fifth cross-sectional shape of the third twist-drivable pin.

* * * * *